United States Patent [19]

Masumoto et al.

[11] Patent Number: 4,950,771
[45] Date of Patent: Aug. 21, 1990

[54] DIHYDROXY COMPOUND

[75] Inventors: Mitsuhito Masumoto; Toshiaki Asoh, both of Toyonaka; Youichirou Ezaki, Osaka; Hiroshi Aibe, Higashiosaka, all of Japan

[73] Assignees: Mitsubishi Gas Chemical Company, Inc., Tokyo; Arakawa Chemical Industries, Ltd., Osaka, both of Japan

[21] Appl. No.: 355,722

[22] Filed: May 19, 1989

[30] Foreign Application Priority Data

May 30, 1988 [JP] Japan .................. 63-132191

[51] Int. Cl.$^5$ .......................... C07D 319/04
[52] U.S. Cl. .................. 549/335
[58] Field of Search ........................ 549/335

[56] References Cited

U.S. PATENT DOCUMENTS 4,739,080 4/1988 Sasaki et al. ............ 549/335
4,754,045 6/1988 Sasaki et al. ............ 549/335
4,769,479 9/1988 Sasaki et al. ............ 549/335

OTHER PUBLICATIONS

Chemical Abstracts, 101-8213w, (1984).

Primary Examiner—Nicky Chan
Attorney, Agent, or Firm—Armstrong, Nikaido, Marmelstein, Kubovcik & Murray

[57] ABSTRACT

This invention provides 3,9-bis[1,1-dimethyl-2-(4'-hydroxybenzoyloxy)ethyl]-2,4,8,10-tetraoxaspiro[5,5]-undecane represented by the formula:

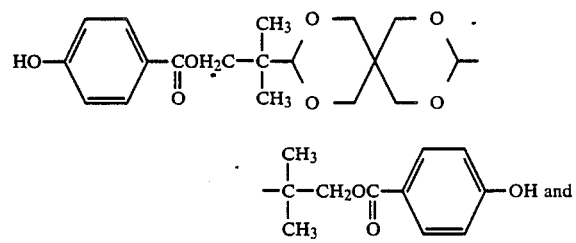

a process for preparing the above compound by a transesterification reaction of 3,9-bis(1,1-dimethyl-2-hydroxyethyl)-2,4,8,10-tetraoxaspiro[5,5]undecane with alkyl 4-hydroxybenzoate.

1 Claim, No Drawings

DIHYDROXY COMPOUND

BACKGROUND OF THE INVENTION

This invention relates to a novel dihydroxy compound and a process for preparing the same.

Dihydroxy compounds have been widely used as a starting material for preparing various synthetic resins, such as polyarylate resin, polycarbonate resin, epoxy resin, polyester resin, etc. However, the resins obtained by using conventional dihydroxy compounds are not satisfactory in thermal and/or mechanical properties, and therefore it is desired to provide a dihydroxy compound capable of giving resins improved in these properties.

SUMMARY OF THE INVENTION

An object of the present invention is to provide a novel dihydroxy compound useful as a starting material for preparing various resins and a process for preparing the compound.

A further object of the invention is to provide a novel dihydroxy compound capable of producing resins having improved thermal and/or mechanical properties and a process for preparing the compound.

These and other objects of the invention will become apparent from the following description.

The dihydroxy compound of the invention is 3,9-bis[1,1-dimethyl-2-(4'-hydroxybenzoyloxy)ethyl]-2,4,8,10-tetraoxaspiro[5,5]undecane represented by the formula (I):

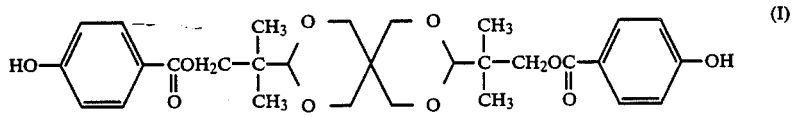

DETAILED DESCRIPTION OF THE INVENTION

The dihydroxy compound of the invention having the formula (I) is useful as a starting material for preparing various synthetic resins such as polyarylate resin, polycarbonate resin, epoxy resin, polyester resin, etc., and is capable of giving resins having improved thermal and/or mechanical properties.

The dihydroxy compound of the invention can be prepared preferably by subjecting to transesterification reaction 3,9-bis(1,1-dimethyl-2-hydroxyethyl)-2,4,8,10-tetraoxaspiro[5,5]undecane represented by the formula (II)

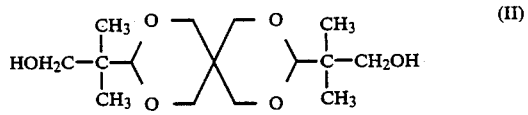

and alkyl 4-hydroxybenzoate in the presence of a transesterification catalyst. The dihydroxy compound of the invention can be prepared also by a direct esterification process in which the compound of the formula (II) is esterified directly with 4-hydroxybenzoic acid in the presence of an acid catalyst such as sulfuric acid, para-toluenesulfonic acid, phosphoric acid, hydrochloric acid or the like. Among these methods the transesterification reaction is preferable in view of reaction velocity, and therefore the following description is made in reference to the transesterification reaction.

In carrying out the transesterification reaction of the present invention, it is preferable to use a specific transesterification catalyst selected from various transesterification catalysts. Preferable catalyst is at least one of organic tin compounds and inorganic tin compounds, which themselves are known as transesterification catalysts. Examples of organic tin compounds are tin oxalate, dibutyltin oxide, dibutyltin maleate, dibutyltin dichloride, tributyltin acetate, tributyltin chloride, trimethyltin chloride, etc. Examples of inorganic tin compounds are stannous oxide, stannic oxide, stannous chloride, etc. These catalysts can be used singly or in admixture with one another.

The amount of the catalyst to be used varies depending on the reaction temperature, but may usually be in the range of about 0.01 to about 10 mole %, preferably about 0.1 to about 5 mole %, based on the mole of 4-hydroxybenzoic acid ester.

Preferably exemplified as 4-hydroxybenzoic acid esters are lower alkyl 4-hydroxybenzoates, more preferably primary lower alkyl 4-hydroxybenzoates, such as methyl 4-hydroxybenzoate, ethyl 4-hydroxybenzoate, n-propyl 4-hydroxybenzoate, isopropyl 4-hydroxybenzoate, n-butyl 4-hydroxybenzoate, isobutyl 4-hydroxybenzoate, etc. Secondary and tertiary alkyl esters having larger steric hindrance, although usable, are liable to retard the reaction.

The esters of 4-hydroxybenzoate can be used in an amount of about 2 to about 4 moles, preferably about 2 to about 2.5 moles, per mole of the 3,9-bis(1,1-dimethyl-2-hydroxyethyl)-2,4,8,10-tetraoxaspiro[5,5]undecane. With less than 2 moles of alkyl 4-hydroxybenzoate, a reduced yield of the desired compound results, whereas more than 4 moles of alkyl 4-hydroxybenzoate used increases the amount of the compound remaining unreacted, not only making the purification procedure complicated but rendering the process uneconomical.

The reaction can be carried out at a temperature of usually about 80 to 240° C, preferably at about 150 to 220° C. The reaction tends to be retarded at a temperature of lower than about 80° C, whereas the reaction temperature of higher than about 240° C is likely to cause undesired decomposition of the contemplated compound. The reaction time is usually about 2 to 48 hours, although suitably determinable in consideration of the reaction temperature and the amount of transesterification catalyst. The reaction is preferably carried out in the presence of an inert solvent such as benzene, toluene, xylene, cyclohexane, tetralin or the like.

The 3,9-bis[(1,1-dimethyl-2-(4'-hydroxybenzoyloxy)ethyl]-2,4,8,10-tetraoxaspiro[5,5]undecane thus obtained can be used as it is or as purified by conventional method such as recrystallization or the like, depending on the application, utility, of the compound.

EXAMPLES

The present invention will be described in more detail with reference to the following examples.

EXAMPLE 1

In a reactor equipped with a stirrer, nitrogen-introducing tube, thermometer, separator and cooling tube were placed 608.3 g (2 moles) of 3,9-bis(1,1-dimethyl-2-hydroxyethyl)-2,4,8,10-tetraoxaspiro[5,5]undecane, 669.5 g (4.4 moles) of methyl 4-hydroxybenzoate, 9.92 g (0.04 mole) of dibutyltin oxide and 100 ml of xylene. The mixture was heated to 200° C while distilling off the xylene and kept with stirring at that temperature for 18 hours, giving 1,132 g of pale yellow semi-crystalline product. The crude product thus obtained was recrystallized from methylethyl ketone, giving 707 g of white crystal having a melting point of 236–239° C. Yield was 65%.

The crystal was identified as 3,9-bis[1,1-dimethyl-2-(4'-hydroxybenzoyloxy)ethyl]-2,4,8,10-tetraoxaspiro[5,5]undecane by elementary analysis, IR absorption spectrum, $^1$H-NMR spectrum and $^{13}$C-NMR spectrum. Elementary analysis

|        | C       | H      |
|--------|---------|--------|
| Calcd. | 63.96%  | 6.66%  |
| Found  | 64.19%  | 6.79%  |

$\nu^{max}$ (KBr): 3285, 1680 cm$^{-1}$ $^1$H-NMR (DMSO-d$_6$)

δppm: 0.95 (6H, s), 0.97 (6H, s), 3.36 (2H, d, J=12Hz), 3.59 (2H, d, J=12Hz), 3.61 (2H, d, J=11Hz), 4.01 (4H, s), 4.29 (2H, d, J=11Hz), 4.37 (2H, s), 6.84 (4H, d, J=9Hz), 7.82 (4H, d, J=9Hz), 10.63 (2H, s).

$^{13}$C-NMR (DMSO-d$_6$)

δppm: 19.40 (q), 19.55 (q), 32.32 (s), 38.54 (s), 68.65 (t), 69.08 (t), 69.52 (t), 104.56 (d), 115.41 (d), 120.42 (s), 131.45 (d), 162.01 (s), 165.50 (s).

EXAMPLE 2

A 669 g quantity of white crystals was produced by following the same procedure as in Example 1 except that 5.39 g (0.04 mole) of stannous oxide was used in place of 9.92 g of dibutyltin oxide. Yield was 61.5%.

The obtained crystals were identical in melting point, IR spectra, $^1$H-NMR spectra and $^{13}$C-NMR spectra of the product with the 3,9-bis[1,1-dimethyl-2-(4'-hydroxybenzoyloxy)ethyl]-2,4,8,10-tetraoxaspiro[5,5]undecane obtained in Example 1.

EXAMPLE 3

A 632 g quantity of white crystals was produced by following the same procedure as in Example 1 except that 13.31 g (0.04 mole) of tributyltin acetate was used in place of 9.92 g of dibutyltin oxide. Yield was 58.1%.

The obtained crystals were identical in melting point, IR spectra, 1H-NMR, 13C-NMR spectra with the 2,2-bis[1,1-dimethyl-2-(4'-hydroxybenzoyloxy)ethyl]-2,4,8,10-tetraoxaspiro[5,5]undecane obtained in Example 1.

EXAMPLE 4

A 592 g quantity of white crystals was produced by following the same procedure as in Example 1 except that 7.58 g (0.04 mole) of stanous chloride was used in place of 9.92 g of dibutyltin oxide. Yield was 54.4%.

The obtained crystals were identical in melting point, IR spectra, 1H-NMR, 13C-NMR spectra with the 2,2-bis[1,1-dimethyl-2-(4'-hydroxybenzoyloxy)ethyl]-2,4,8,10-tetraoxaspiro[5,5]undecane obtained in Example 1.

EXAMPLE 5

A 685 g quantity of white crystals was produced by following the same procedure as in Example 1 except that 854.3 g (4.4 moles) of butyl 4-hydroxybenzoate was used in place of 669.5 g of methyl 4-hydroxybenzoate. Yield was 63.0%.

The obtained crystals were identical in melting point, IR spectra, 1H-NMR, 13C-NMR spectra with the 2,2-bis[1,1-dimethyl-2-(4'-hydroxybenzoyloxy)ethyl]-2,4,8,10-tetraoxaspiro[5,5]undecane obtained in Example 1.

EXAMPLE 6

A 668 g quantity of white crystals was produced by following the same procedure as in Example 1 except that 792.7 g (4.4 moles) of isopropyl 4-hydroxybenzoate was used in place of 669.5 g of methyl 4-hydroxybenzoate. Yield was 61.5%.

The obtained crystals were identical in melting point, IR spectra, 1H-NMR, 13C-NMR spectra with the 2,2-bis[1,1-dimethyl-2-(4'-hydroxybenzoyloxy)ethyl]-2,4,8,10-tetraoxaspiro[5,5]undecane obtained in Example 1.

We claim:

1. 3,9-bis[1,1-dimethyl-2-(4'-hydroxybenzoyloxy)ethyl]-2,4,8,10-tetraoxaspiro[5,5]undecane represented by the formula:

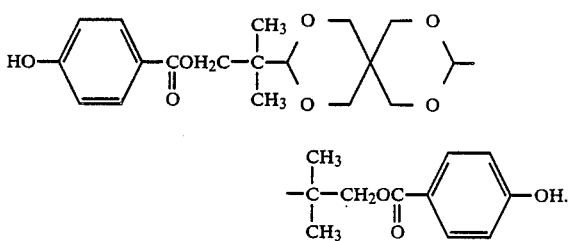

UNITED STATES PATENT AND TRADEMARK OFFICE
CERTIFICATE OF CORRECTION

PATENT NO. : 4,950,771
DATED : August 21, 1990
INVENTOR(S) : MASUMOTO et al

It is certified that error appears in the above-identified patent and that said Letters Patent is hereby corrected as shown below:

On the cover page, Item [75], "Mitsuhito Masumoto" should read --Mitsuhiko Masumoto--.

Signed and Sealed this

Tenth Day of December, 1991

Attest:

HARRY F. MANBECK, JR.

*Attesting Officer*     *Commissioner of Patents and Trademarks*